United States Patent [19]

Hendricks

[11] Patent Number: 4,877,605

[45] Date of Patent: Oct. 31, 1989

[54] FOOT DEODORANT

[76] Inventor: David Hendricks, Rte. 5, Box 354, Pickens, S.C. 29671

[21] Appl. No.: 283,546

[22] Filed: Dec. 12, 1988

[51] Int. Cl.$^4$ .............................................. A61K 7/32
[52] U.S. Cl. ..................................................... 424/65
[58] Field of Search ........................ 424/65, 66, 67, 68

[56] References Cited

U.S. PATENT DOCUMENTS 4,719,101 1/1988 Morrison ................................ 424/65
4,777,034 11/1988 Olivier et al. .......................... 424/67

*Primary Examiner*—Dale R. Ore
*Attorney, Agent, or Firm*—Bailey & Hardaway

[57] ABSTRACT

A foot deodorant comprising a combination of boric acid, hydrogen peroxide, sodium chloride and alcohol diluted in water. Measured proportions of the above substances act as an antiseptic which inhibits the activity of microorganisms, and also neutralizes existing acids and fats on the surface of the skin. By controlling the reaction of the odor-causing microorganisms with the naturally occurring fats on the surface of the foot, foot odor can be eliminated or significantly reduced.

6 Claims, No Drawings

FOOT DEODORANT

BACKGROUND OF THE INVENTION

The subject invention relates generally to a composition of matter and, more specifically, to a composition for control of human foot odor.

The search for control of foot odor has been the subject of a significant amount of interest for many years. Because perspiration has been associated with the creation of foot odor, much of the effort has been directed toward preparation of astringent or perspiration-inhibiting compositions in an effort to interfere with that element of the chain of events leading up to the generation of foot odor. For many years numerous chemical compounds have been used for the purpose of inhibiting persperation associated with body odor in general. Although a specific compound used may be more or less effective than selective other compounds, many of the chemicals tested have certain shortcomings that have caused them to be less successful from a commercial standpoint. Some of the compounds have been found to stain clothing material with which it comes into contact, and other chemical compounds have been found to cause skin irritation due in part to excess acidity upon contact with the skin.

The most commonly utilized cosmetic astringent for perspiration control has been aluminum chloride, which itself is highly effective as an astringent and maintains its qualities over a longer period of time than most other chemical compounds. Although aluminum chloride does have the disadvantage of excessive acidity, that problem has been reduced by the addition of specific nitrogenous compounds which tend to make the astringent less acid and, therefore, much more acceptable from a cosmetic standpoint.

Notwithstanding the commercial success of aluminum chloride compounds for body odor, especially odor arising from under the arms, such antiperspirants have not proven widely successful in the treatment of foot odor. Because shoes, socks and stockings trap the moisture and heat created by perspiration and exertion, a unique environment is created for the incubation of odor causing bacteria on the surface and in the pores of the skin of the foot. These bacteria and other organisms break down the fats produced by the sebaceous glands in the feet. Foot odor is created when these fats are broken down.

SUMMARY OF THE INVENTION

It is an important object of the subject invention to create a compound which is effective in killing and inhibiting the action of odor causing microorganisms on the surface of the feet.

Another important object of the invention is to create a chemical compound effective in controlling foot odor which is mild enough to pose no irritation to the skin of the foot.

These as well as other objects are accomplished by a composition comprising the combination of boric acid, hydrogen peroxide, sodium chloride and alcohol diluted in water.

DETAILED DESCRIPTION

In accordance with this invention, it has been found that measured proportions of the will act as an antiseptic which inhibits the activity of microorganisms, and will also neutralize existing acids and fats on the surface of the skin. By controlling the reaction of the odor-causing microorganisms with the naturally occurring fats on the surface of the foot, foot odor can be eliminated or significantly reduced.

In order that those skilled in the art may more fully understand the manner in which the subject invention may be practiced, relative examples of the invention are described below. These examples are intended to be illustrative only, and are not intended to be limitative of the breadth of the invention in any way. For example, the proportions of the ingredients may be varied, different combinations of ingredients may be employed, and other changes may be made without departing from the principles of the invention as herein described.

Any combination of boric acid, hydrogen peroxide, sodium chloride and alcohol added to a solution of water can be effective in controlling foot odor.

It has been found that the preferred composition of the invention comprises about 7% boric acid, about 2% hydrogen peroxide, about 0.005% sodium chloride and about 0.005% alcohol with water comprising the balance of the composition. Either methanol or ethanol may be used as the alcohol component.

The described deodorant composition is applied only to a foot which has first been cleaned and dried to eliminate, as much as possible, the oils and perspiration which may be present.

The deodorant composition may be applied in the form of a spray or may be applied by other means such as with an absorbant pad or roll-on dispenser. It may be found necessary to reapply the deodorant to the foot periodically, depending upon the requirements of the individual user and the environment in which the foot is placed.

It has surprisingly been found that the composition of this invention also alleviates fungus infections of the toe nails as well. This surprising result also alleviates the ingrown nail problem frequently associated with nail fungus problems.

It is thus seen that the deodorant composition of this invention provides a composition which creates a compound which is effective in killing and inhibiting the action of odor causing microorganisms on the surface of the feet and to create a chemical compound effective in controlling foot odor which is mild enough to pose no irritation to the skin of the foot.

As many variations will become apparent to those of skill in the art from a reading of the description, such variations are embodied within the spirit and scope of the invention as defined by the following appended claims.

What is claimed is:

1. A foot deodorant, comprising:
boric acid;
hydrogen peroxide;
sodium chloride; and
alcohol;
balance water.

2. A foot deodorant, comprising:
about 7% boric acid;
about 2% hydrogen peroxide;
about 0.005% sodium chloride; and
about 0.005% alcohol;
balance water.

3. The foot deodorant composition of claim 1 consisting essentially of boric acid, hydrogen peroxide, sodium chloride and alcohol, balance water.

4. The foot deodorant composition of claim 2 consisting essentially of about 7% boric acid, about 2% hydrogen peroxide, about 0.005% sodium chloride, and about 0.005% alcohol, balance water.

5. A foot deodorant as in claim 1 wherein said alcohol is methanol.

6. A foot deodorant as in claim 1 wherein said alcohol is ethanol.